(12) United States Patent
Scalise (10) Patent No.: US 10,556,061 B2
(45) Date of Patent: Feb. 11, 2020

(54) DEVICE, KIT, AND METHOD FOR PRODUCING MEDICALLY-DELIVERABLE INTRAVENOUS SOLUTION

(71) Applicant: ODSS Holdings, LLC, Greenville, SC (US)

(72) Inventor: Michael B. Scalise, Greenville, SC (US)

(73) Assignee: ODSS Holdings, LLC, Greenville, SC (US)

( * ) Notice: Subject to any disclaimer, the term of this patent is extended or adjusted under 35 U.S.C. 154(b) by 0 days.

(21) Appl. No.: 16/151,502

(22) Filed: Oct. 4, 2018

(65) Prior Publication Data

US 2019/0282755 A1 Sep. 19, 2019

Related U.S. Application Data

(60) Provisional application No. 62/643,910, filed on Mar. 16, 2018.

(51) Int. Cl.
| | |
|---|---|
| *A61M 5/168* | (2006.01) |
| *A61M 5/142* | (2006.01) |
| *A61M 5/165* | (2006.01) |
| *A61J 1/20* | (2006.01) |
| *B01F 3/08* | (2006.01) |
| *A61J 3/00* | (2006.01) |
| *A61M 5/14* | (2006.01) |
| *A61J 1/10* | (2006.01) |

(52) U.S. Cl.
CPC .......... *A61M 5/1689* (2013.01); *A61J 1/2003* (2015.05); *A61J 3/002* (2013.01); *A61M 5/142* (2013.01); *A61M 5/1408* (2013.01); *A61M 5/165* (2013.01); *A61M 5/16827* (2013.01); *B01F 3/08* (2013.01); *A61J 1/10* (2013.01); *A61J 1/2093* (2013.01); *A61M 5/16854* (2013.01); *A61M 5/16877* (2013.01); *A61M 2005/14272* (2013.01); *A61M 2205/3324* (2013.01); *A61M 2205/3368* (2013.01); *A61M 2230/30* (2013.01)

(58) Field of Classification Search
CPC .... A61M 5/1689; A61M 5/142; A61M 5/165; A61J 1/2003
USPC ........................................................ 604/251
See application file for complete search history.

(56) References Cited

U.S. PATENT DOCUMENTS

| | | | |
|---|---|---|---|
| 5,108,372 A * | 4/1992 | Swenson | A61M 5/16886 604/113 |
| 9,119,915 B2 * | 9/2015 | Kawamura | A61M 5/1407 |
| 2002/0154567 A1 | 10/2002 | Usher | |
| 2005/0171501 A1 | 8/2005 | Kelly | |
| 2012/0043269 A1 | 2/2012 | Shariff | |

(Continued)

OTHER PUBLICATIONS

Search Report and Written Opinion for International Application No. PCT/US2019/022682, dated Jun. 18, 2019.

*Primary Examiner* — Phillip A Gray
(74) *Attorney, Agent, or Firm* — JK Intellectual Property Law, PA (57) ABSTRACT

A device, kit, and method for producing medically-deliverable intravenous solution may include supplying a liquid to a housing, pumping the liquid through the housing while purifying the liquid, metering concentrated intravenous solution into the liquid to create a medically-deliverable intravenous solution, and dispensing the medically-deliverable intravenous solution.

26 Claims, 6 Drawing Sheets

(56) References Cited

U.S. PATENT DOCUMENTS

2012/0053512 A1* 3/2012 Muse .................... A61M 39/16
604/21
2015/0129499 A1* 5/2015 Bene ....................... A61M 1/16
210/647

* cited by examiner

DEVICE, KIT, AND METHOD FOR PRODUCING MEDICALLY-DELIVERABLE INTRAVENOUS SOLUTION

CROSS-REFERENCE TO RELATED APPLICATION

The present application is a Non-Provisional Patent Applications and claims priority to U.S. Provisional Patent Application Ser. No. 62/643,910, filed Mar. 16, 2018, which is incorporated by reference herein.

TECHNICAL FIELD

The present disclosure relates generally to a kit and method for delivering an intravenous solution. In other aspects, the present disclosure relates to a kit and method employing concentrated solutions or other materials for intravenous use.

BACKGROUND

Intravenous (IV) infusion of fluids into a patient's bloodstream is a common medical procedure. Fluids that are typically administered intravenously include "normal" saline solutions, hypertonic saline solutions, balanced (crystalloid) solutions, colloid solutions, glucose solutions, blood-based products, blood substitutes, plasma solutions, and others. Often while an infusion is administered other medical fluids such as drugs may be introduced into the infusion.

Some common IV systems include a reservoir, and an infusion kit with a dripper, a tube, and a catheter with an IV needle. The reservoir, also sometimes called an IV bag, holds a quantity of the fluid to be infused. The reservoir is held above the patient so that the liquid is fed via gravity. The IV fluid passes from the reservoir to the dripper to the tube and into the patient via the catheter. The rate of flow of the fluid (called a drip rate) may be controlled by the dripper.

By its very nature, IV solutions are often water-based liquid solutions. Accordingly, the size, weight, density and resulting bulkiness of IV bags lead to issues with production, transportation, storage, and inventory maintenance. Such issues arise both in institutional settings, such as in hospitals, clinics, schools, colleges, etc. Such issues are perhaps more troublesome in mobile settings, such as use by fire and rescue squads, military personnel, hunters and or others in remote locations distant from medical facilities, etc.

Thus, while existing IV solution delivery devices, systems, and methods generally work for their intended purposes, improvements to such devices and/or methods that were less cumbersome, and/or that addressed one of the drawbacks of existing devices, systems, or methods, and/or other issues, would be welcome.

SUMMARY

According to certain aspects of the disclosure, a device for producing medically-deliverable intravenous solution from a source of liquid may include, for example, a housing; a conduit connected to the housing having an inlet and an outlet, the inlet attachable to the source of liquid; a purification device located along the conduit downstream of the inlet for purifying the liquid; a pump within the housing for pumping the liquid through the conduit; a container connectable to the housing holding a concentrated intravenous solution, the container having an outlet in communication with the conduit; a metering device for dispensing the concentrated intravenous solution from the container into the liquid; and a controller connected to the housing for controlling the pump and the metering device so as to create the medically-deliverable intravenous solution and deliver the medically-deliverable intravenous solution to the outlet. Various options and modifications are possible.

For example, the device may include at least one additional container for supplying a medical liquid and at least one additional metering device for dispensing the medical liquid from the at least one additional container into the liquid. The device may also further include a liquid supply container for supplying the liquid, the liquid supply container having an outlet connected to the inlet of the conduit. If so, the liquid supply container may be external to the housing. Also, the inlet of the conduit is configured for an attachment to a regional water supply or to an environmental source.

The device may further include a sensor for sensing a flow of the liquid in the conduit, and the sensor may send a signal to the controller, the controller operating the pump and the metering device based on the signal to thereby create the medically-deliverable intravenous solution. The sensor may be a flow rate sensor.

The device may further include a mixing chamber along the conduit downstream of the purifying device and the metering device and upstream of the outlet, the liquid pumped by the pump and the concentrated intravenous solution dispensed by the metering device being housed in the mixing chamber before passing through the outlet. The device may also further include a mixing channel between the metering device and the mixing chamber, the pump pumping the liquid into and the metering device dispensing the concentrated intravenous solution into the mixing channel. A filter may be provided along the conduit between the mixing chamber and the outlet, and may provide a filtration particle size of about 0.2 microns or smaller.

The device may include an intravenous infusion kit in communication with the outlet, and the intravenous infusion kit may include a catheter, an infusion line attached to the catheter, and a drip chamber attached to the infusion line. The drip chamber may include a connector for attachment to the outlet.

The housing may be configured for removable attachment of the container and replacement of the container when the all concentrated intravenous solution in the container has been dispensed by the metering device.

A kit may be provided including any of the devices above and at least two of the containers of the concentrated intravenous solution. If so, at least one additional container may be provided for supplying a medical liquid and at least one additional metering device may be provided for dispensing the medical liquid from the at least one additional container into the liquid.

The housing may support the conduit, the purifying device, the pump, the container, the metering device, and the controller in a portable handheld unit, in a portable wheeled unit, or in a unit fixed to a building structure.

The medically-deliverable intravenous solution may include at least one of a normal saline solution, a hypertonic saline solution, a crystalloid solution, a plasma volume expander, a drug, and a plasma solution.

The concentrated intravenous solution may include at least one of a concentrated normal saline solution, a concentrated hypertonic saline solution, and a concentrated crystalloid solution, a concentrated plasma volume expander, a concentrated drug, and a concentrated plasma solution including separately held freeze-dried plasma particles and a plasma solvent.

The container may include a first compartment and a second compartment, the concentrated intravenous solution in the form of freeze-dried plasma particles held in the first compartment and a plasma solvent held in the second compartment. If so, the container may include an actuation device, such as a spring-loaded plunger actuated by a signal from the controller, for introducing the plasma solvent into the freeze-dried plasma particles to create a concentrated plasma solution to be dispensed by the metering device.

The purifying device may include a filter, which may have multiple sequential stages, wherein a more downstream one of the stages is configured for a finer filtration than a more upstream one of the stages. The filter may provide a filtration particle size of about 0.2 microns or smaller. Additionally or alternatively, the purifying device may include a UV radiation source.

The controller may be configured to actuate the pump but not the metering device to thereby cleanse the conduit between uses of the device.

The device may further include a P.H. adjustment chamber in the housing, with at least one additional container supplying a P.H. adjusting liquid for adjusting the P.H. of the medically-deliverable intravenous solution. The P.H. adjusting liquid may include HCl, and the P.H. adjustment chamber may be upstream of the mixing chamber. A sensor may be employed in communication with the controller for sensing a P.H. of the liquid supplied by the source of liquid, the controller then causing the at least one additional container to dispense the P.H. adjusting liquid based on a sensed P.H communicated by the sensor.

The device may further including a heating device located in the housing so as to heat at least the liquid upstream of the outlet. For example, the heating device may heat the medically-deliverable intravenous solution in the mixing chamber. A sensor may be employed in communication with the controller for sensing a temperature of the medically-deliverable intravenous solution, the controller causing the heating device to provide heat based on a sensed temperature communicated by the sensor.

The device may further include an infusion pump located in the housing for pumping the medically deliverable intravenous solution out of the outlet. Also, the intravenous infusion kit may include a sensor in communication with the controller for determining a blood pressure of a patient by sensing a line pressure of the medically-deliverable intravenous solution in the infusion kit, the controller causing the device to display the determined blood pressure of the patient on a display. An input-output device may be employed in communication with the housing for receiving input from a user and for providing operational data information to the user.

According to other aspects of the disclosure, a method of producing a medically-deliverable intravenous solution may include, for example, the steps of supplying a liquid to a housing; pumping the liquid through the housing while purifying the liquid; metering a concentrated intravenous solution into the liquid so that the concentrated intravenous solution and the liquid are mixed to create a medically-deliverable intravenous solution; and dispensing the medically-deliverable intravenous solution. As above, various options and modifications are possible.

For example, the supplying step may include supplying the liquid from a liquid supply container, or a regional water supply, or an environmental source.

The method may further include including receiving the concentrated intravenous solution and the liquid in a mixing chamber after the pumping and metering steps and before the dispensing step, and may further include transferring the concentrated intravenous solution and the liquid along a mixing channel before receiving the concentrated intravenous solution and the liquid in the mixing chamber. The method may also include filtering the medically-deliverable intravenous solution as it exits the mixing chamber during the dispensing step, and the filtering may provide a filtration particle size of about 0.2 microns or smaller.

The method may further including metering a medical liquid into the liquid. The method may include including administering the medically-deliverable intravenous solution to a patient, storing the medically-deliverable intravenous solution, and/or storing the housing at a first location, moving the housing to a second location where a patient is located, and administering the medically-deliverable intravenous solution to the patient at the second location. The second location may be remote from a medical care facility.

The housing may be located at a medical care facility where medically-deliverable intravenous solution is regularly administered to patients, and the dispensing may include administering immediately upon creation the medically-deliverable intravenous solution to the patients at the medical care facility. Also, the housing may be located at a medical care facility where medically-deliverable intravenous solution is regularly administered to patients, and the dispensing may include creating an inventory of medically-deliverable intravenous solution for later administering to the patients at the medical care facility. Further, the housing may be located at a facility that supplies medical care facilities where medically-deliverable intravenous solution is regularly administered to patients, and the dispensing may include creating an inventory of medically-deliverable intravenous solution at the facility for delivery to the medical care facilities for later administering to the patients at the medical care facility.

In the method, the medically-deliverable intravenous solution may include at least one of a normal saline solution, a hypertonic saline solution, a crystalloid solution, a plasma volume expander, a drug, and a plasma solution. Also, the concentrated intravenous solution may include one of a concentrated normal saline solution, a concentrated hypertonic saline solution, a concentrated crystalloid solution, a concentrated plasma volume expander, a concentrated drug, and a concentrated plasma solution including separately held freeze-dried plasma particles and a plasma solvent. The metering step may include introducing a plasma solvent into freeze-dried plasma particles to meter a concentrated plasma solution.

The liquid may be purified using a filter, and if so, the filter may have multiple sequential stages, wherein a more downstream one of the stages is configured for a finer filtration than a more upstream one of the stages, and/or the filter may provide a filtration particle size of about 0.2 microns or smaller. The liquid may also or instead be purified using a UV radiation source.

The method may further include repeating the pumping step without the metering step to cleanse the housing between instances of performing the method of producing a medically-deliverable intravenous solution, wherein the dispensing step includes disposing of the pumped liquid.

The method may further include adjusting a P.H. of the supplied liquid, and if so the adjusting of the P.H. of the supplied liquid may include adding HCl to the supplied liquid in a P.H. adjustment chamber and/or sensing a P.H. of the supplied liquid before adjusting a P.H. of the supplied liquid based on the sensed P.H of the supplied liquid.

The method may also further include supplying heat upstream of the outlet, and if so the supplying heat step may include supplying heat to the medically-deliverable intravenous solution in the mixing chamber, and/or sensing a temperature of the medically-deliverable intravenous solution before supplying heat based on the sensed temperature of the medically-deliverable intravenous solution.

The dispensing step may include pumping the medically deliverable intravenous solution out of the mixing chamber. The method may further include administering the medically-deliverable intravenous solution to a patient using an intravenous infusion kit. If so, the method may also include determining a blood pressure of a patient by sensing a line pressure of the medically-deliverable intravenous solution in the infusion kit, and displaying the determined blood pressure of the patient on a display. The method may also include receiving input from a user and providing operational data information to the user via an input-output device.

BRIEF DESCRIPTION OF THE DRAWINGS

These and other features of the disclosure will be more readily understood from the following detailed description of the various aspects of the disclosure taken in conjunction with the accompanying drawings that depict various aspects of the disclosure.

DETAILED DESCRIPTION

Detailed reference will now be made to the drawings in which examples embodying the present disclosure are shown. The detailed description uses numeral and letter designations to refer to features in the drawings. Like or similar designations in the drawings and description have been used to refer to like or similar parts of the disclosure.

The drawings and detailed description provide a full and enabling description of the disclosure and the manner and process of making and using it. Each embodiment is provided by way of explanation of the subject matter not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

Generally speaking, the present disclosure is directed to aspects of a device, kit, and method for producing a medically-deliverable intravenous solution. The solution may be infused into a patient immediately upon creation, or it may be stockpiled for later use. The device may be used for manufacture of intravenous liquid (i.e., creation of IV solution in bulk or in individual use bags) from concentrate at a remote site where liquid such as water is readily available, thereby simplifying transportation by reducing transportation requirements to concentrate and device rather than the full volume of water. The device may be used at clinics, hospitals, military installations, vehicles or ships, emergency vehicles, in the outdoors, for example by hunters, hikers, etc., at worksites, for example in factories, quarries, railroads, etc. The device may be configured to be small and readily transportable, to be made larger and mobile (for example mounted on a wheeled cart for rolling between rooms in a medical facility), or to be fixed in place adjacent a connection to a source of water. The concentrated solutions may be provided for saline, drugs or any other intravenously-deliverable liquid, creatable on demand or in advance from a source of fluid (e.g., water). The concentrated solutions can be supplied in cartridges insertable into the device. Multiple different types of cartridges can be supplied in a kit. Multiple cartridges of saline can be provided as needed to provide a base fluid into which drugs or other liquids can be added. One or more IV infusion kits may be provided with the device in kit form. If the liquid source is already medically deliverable (i.e., is a source of saline solution), the device may be use to add medication or other liquids to the saline solution. Thus, many options and applications are possible in view of the present disclosure.

Figure 1:
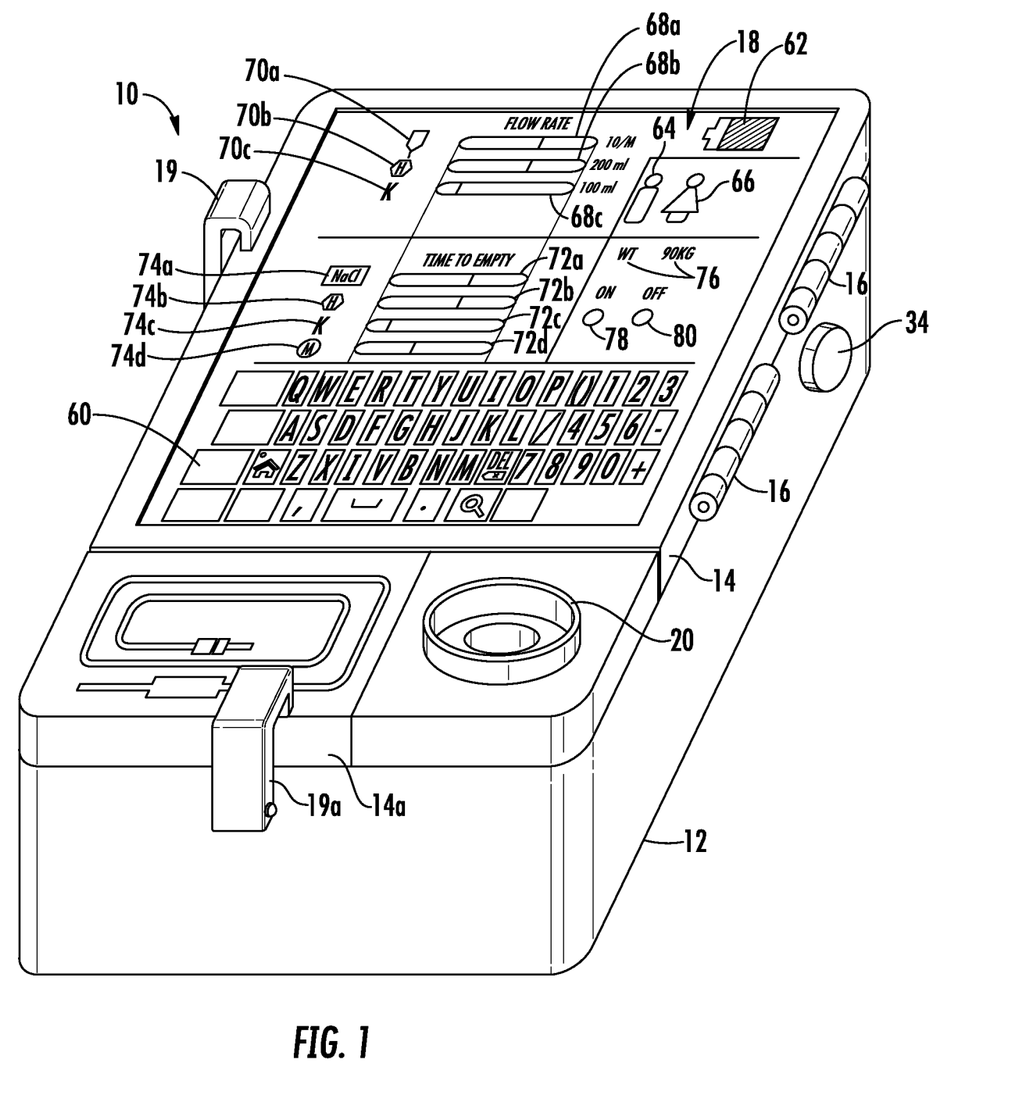
FIG. 1 is an isometric view of one version of a device for producing a medically-deliverable intravenous solution according to certain aspects of the disclosure, with front covers of the device in a closed position.
Figure 2:
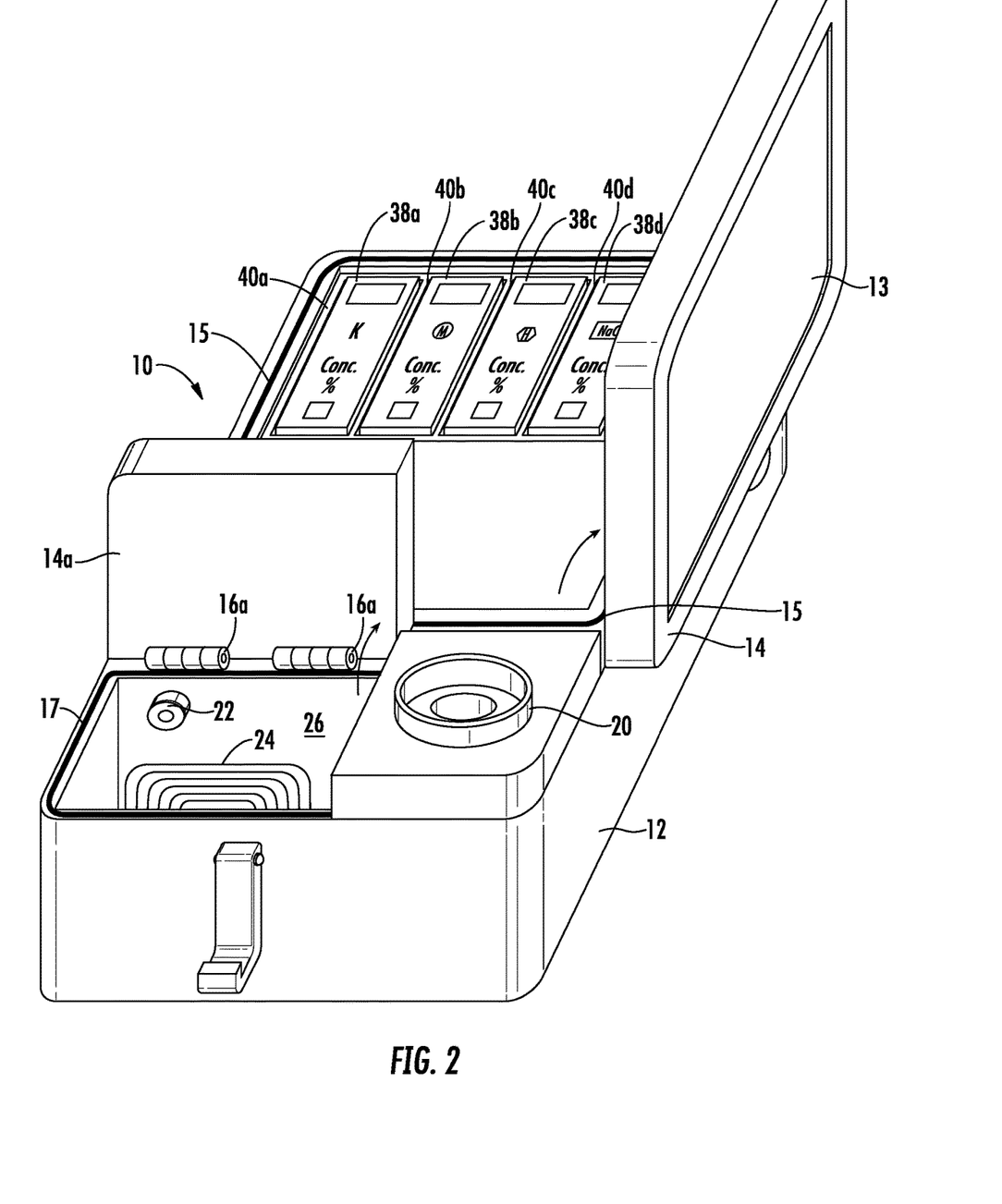
FIG. 2 is an isometric view of the device of FIG. 1, with the front covers in an opened position.

With reference to the figures, a device 10 includes a housing 12 having an openable lid 14 which may be connected by hinges 16. As shown in FIGS. 1 and 2, hinges 16 are on the right side of front of housing 12, but they could alternatively be on the top side, bottom side, or left side. Much of lid 14 includes a display 18, which may be a touch screen input-output device. A liquid inlet 20 and a liquid outlet 22 are provided on housing 12. Liquid inlet 20 may employ any suitable connection or adapter such as a snap fit, luer lock, threading, "camelback" type connector, etc., for connection to one or more types of sources (S1-S3) of liquid. As non-limiting examples, S1 may be a transportable container of liquid, S2 may be a municipal or other regional source of liquid with a fixed outlet, and S3 may be an environmental source of liquid.

Liquid outlet 22 of housing 12 may employ various connectors, and may be configured to connect to a conventional IV infusion kit 24, one or more of which may be supplied in a compartment 26 within housing 12. A secondary lid 14a may be provided for compartment 26, and it may be mounted via its own hinges 16a, if desired, to selectively cover compartment 26. Hinges 16a could be located on any edge of compartment 26. Liquid outlet 22 may be arranged perpendicularly and linearly downward in housing 12 (as shown) but may also be angled or oriented as desired for convenient access. It is generally expected that device 12 would be used with outlet 22 functioning as a passive IV drip infusion source, so any orientation that would allow such function would be suitable. To provide an environmental seal, O-rings 15 and 17 may be provided on housing 12 to seal around lids 14, 14a when closed. Each lid 14, 14a may include a latch 19, 19a (or equivalent closure mechanism) to selectively maintain the lids in a closed and sealed state or to allow the lids to be opened when desired.

A flow path through housing 12 between inlet 20 and outlet 22 can be considered a conduit through housing 12. A number of elements within housing 12 act on, modify, or add to fluid flowing through the conduit, as noted below, to create a medically-deliverable intravenous solution from a source of liquid supplied to inlet 20 and one or more concentrated liquids added within housing 12. For example, as shown in FIGS. 3-7, one or more removable containers 38 may be provided for supplying a concentrated liquid.

A pump 28 is provided to draw fluid through inlet 20 and pass it though a purification device 30. Pump 28 and purification device 30 should have a flow rating sufficient for the purpose intended for device 10 (i.e., on demand supply to a patient vs advance stockpiling). Purification device 30 may include one or more filters, or may be a multi-stage filter 30*a* (e.g., a two to four stage filter) sufficient to provide water of necessary sterility for infusion. A final filtration size may be no greater that 0.2 microns. Filter 30*a* may include graphene or other suitable materials.

Purification device 30 may also include an irradiative sterilization device, such as a UV source 30*b* (such as an LED or other source) directing UV radiation onto a flow of pumped fluid through a UV-transmissive element (i.e., conduit, exposed area, etc.). UV light is sometimes classified into three wavelength ranges: UV-C, from about 200 nanometers (nm) to about 280 nm; UV-B, from about 280 nm to about 320 nm; and UV-A, from about 320 nm to about 400 nm. UV light, and in particular, UV-C light is "germicidal," i.e., it deactivates the DNA of bacteria, viruses and other pathogens and thus destroys their ability to multiply and cause infections and diseases.

If desired, purification device 30 can include some or all of filter(s) 30*a* and UV-irradiation elements 30*b* in a single unit, replaceable between patients, after a certain liquid volume of filtration or time of usage, or after clogging is noted or electronically detected, etc. Different types of filter(s) 30*a* and/or UV-irradiation elements 30*b* can be designed having different filtering and/or irradiation characteristics in view of the source of liquid (i.e., a city water source, a container of distilled or purified water, an unpurified environmental source, etc.), the locale of use, etc.

Pump 28 may be powered via a power source 32 such as a battery, or an AC or DC connection. A sealed on-off switch or button 34 may be provided to activate power source 32 for device 10. A controller 36 may be provided in housing 12 including conventional integrated circuit, processor, memory holding data and a control program, etc., mounted for example on one or more printed circuit boards. Controller 36 is connected to the power source 32 and other elements of device 10 via conventional electrical connections (not shown for clarity). One or more sensors (not shown) may measure and indicate to controller 36 flow rate, temperature, liquid type, liquid concentration, liquid fullness, etc., as desired. Memory of controller 36 may include lookup tables for each potential concentrated liquid to be used in device 10, so that flow rates for creation and infusion of the solutions, concentrate levels, liquid source type, dosages for types of injuries, body type, body size or weight, gender of patient, etc., may be preloaded so that One or more containers 38 may be provided, connectable to housing 12 and each holding a concentrated intravenous solution. As shown, four containers 38*a-d* are inserted into openings 40*a-d* in housing 12. Each container 38 may (but need not) hold a different concentrated liquid. For example, container 38*a* may hold a concentrated saline solution; container 38*b* may hold a blood plasma volume expander such as Hextend®; container 38*c* may include a drug such as morphine; and container 38*d* may include a liquid such as potassium chloride. However, containers 38 may include any desired substance deliverable via intravenous infusion, such as freeze-dried plasma and plasma solvent, as described below.

Figure 3:
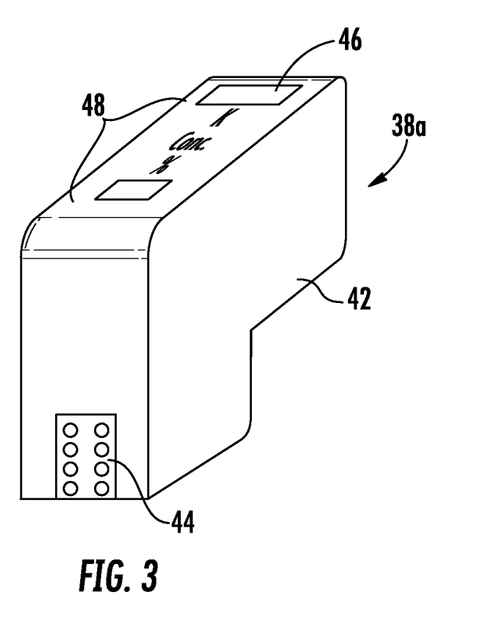
FIG. 3 is a front isometric view of one of the container insertable into the device of FIG. 1.
Figure 4:
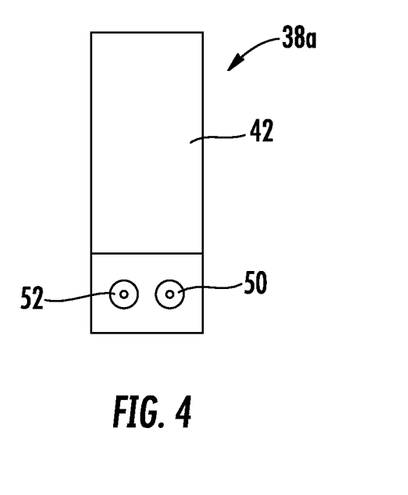
FIG. 4 is a rear view of the container of FIG. 3.
Figure 5:
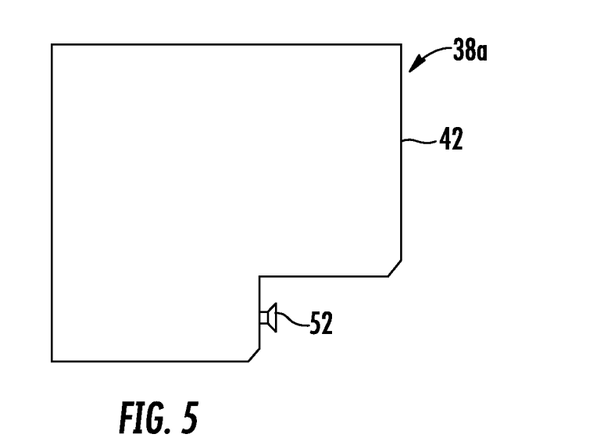
FIG. 5 is a side view of the container of FIG. 3.

Each container 38 may be in the form of an insertable and if desired, disposable or refillable, cartridge similar in concept to a printer cartridge. As shown in FIGS. 3-5 cartridge 38*d* may include a housing 42 with electrical connections 44 communicable with controller 36, a window 46 for visual inspection of an amount of liquid in housing 42, indicia 48 for indicating to a user information such as the substance in housing, the concentration, the date of manufacture, the batch number, and/or a computer readable code such as a QR code, barcode or the like, for further information on the container, the substance or use instructions. Container 38 also includes an outlet 50 and optionally an inlet 52. Outlet 50 includes an electronically controlled valve to meter a defined amount of concentrate when signaled by controller 36.

Cartridges may be used to form a saline solution such as what is conventionally called a "Normal Saline" (NS), a solution of 0.9% w/v of NaCl, about 300 mOsm/L. Less commonly, this solution is (perhaps inaccurately) referred to as physiological saline or isotonic saline. NS is used frequently in intravenous drips (IVs) for patients who cannot take fluids orally and have developed or are in danger of developing dehydration or hypovolemia. NS is typically the first fluid used when hypovolemia is severe enough to threaten the adequacy of blood circulation and has long been believed to be the safest fluid to give quickly in large volumes. Cartridges may also dispense "Half Normal Saline," which is a similar product but with a 0.45% w/v of NaCl, or a "Hypertonic Saline." Hypertonic Saline (HTS) refers to any saline solution with a concentration of NaCl higher than physiologic (0.9%). Commonly used preparations include 2%, 3%, 5%, 7%, and 23% NaCl. Cartridges 28 can also dispense a Lactated Ringer Solution, which is a mixture of sodium chloride, sodium lactate, potassium chloride, and calcium chloride in water.

Figure 6:
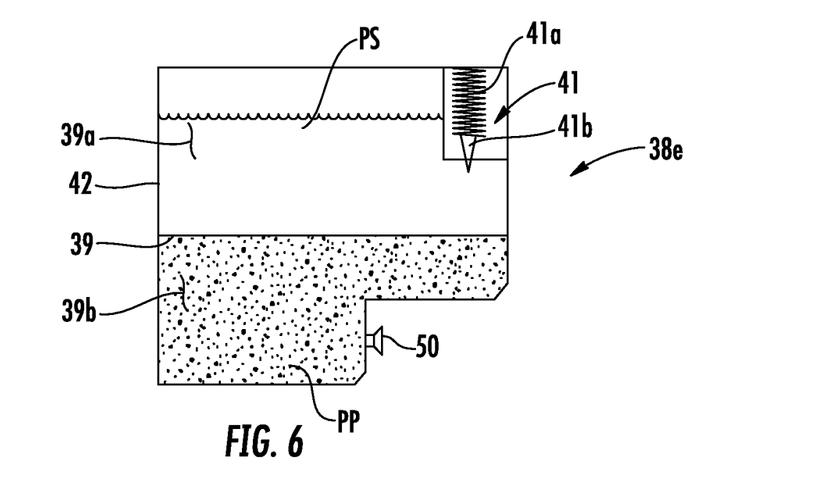
FIG. 6 is a side schematic view of an alternate container for dispensing a concentrated plasma solution from freeze-dried plasma and plasma solvent in a pre-actuated condition.
Figure 7:
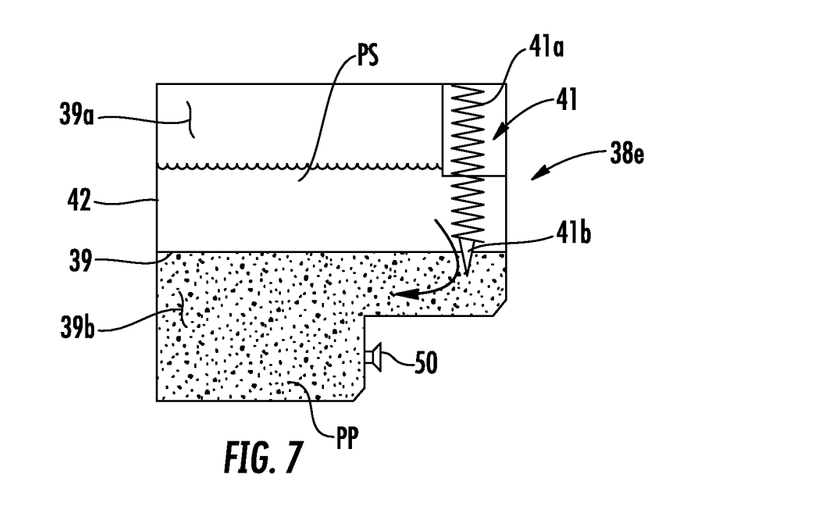
FIG. 7 a side schematic view as in FIG. 6, showing the alternate container in an actuated condition.

As shown in FIGS. 6 and 7, alternate cartridge 38*e* may be provided for dispensing a concentrated plasma solution. Cartridge 38*e* may be externally shaped similarly to or scaled to cartridges 38*a-d*, and may be controlled using electrical connections 44. Cartridge 38*e* includes an internal divider 39 in the form of a wall, a non-permeable membrane or the like dividing cartridge 38*e* into an upper compartment 39*a* and a lower compartment 39*b*. Freeze dried plasma particles PP are held in lower compartment 39*b*, and a plasma solvent PS capable of reconstituting the particles into a plasma solution is held in upper compartment 39*a*.

A mechanism for mixing plasma particles PP and plasma solvent PS, preferably within cartridge 38*e*, is provided. As illustrated, container 38*e* includes a spring-loaded actuation 41 device for introducing plasma solvent PS into the plasma particles PP. Actuation device 41 includes a compression spring 41*a* (preloaded in the condition shown in FIG. 6) attached to a piercing member 41*b* such as a needle, blade, or multiple sharps for piercing divider 39 when signaled to do so by controller 36. A plunger (not shown) may be provided to urge at least some of plasma solvent PS through divider 39, although plasma solvent PS may flow into compartment 39*b* partially or wholly via gravity flow. FIG. 7 shows cartridge 38*e* after actuation of actuation device 41 as plasma solvent PS is flowing into compartment 39*b* and reconstituting plasma particles PP into a concentrated plasma solution, which once reconstituted is then metered through outlet 50.

Each outlet 50 is employed for metering the respective concentrated solution into the flow path within housing into mixing chamber 54 and then ultimately further to outlet 22 of housing 12. If desired, an optional mixing channel 55 may be provided along and into mixing chamber 54, so that pumped liquid and metered concentrate first travels along the mixing channel to begin the mixing process before entering the mixing chamber. Use of mixing channel 55 and mixing chamber 54 assist in creating a uniform infusion, however, an additional agitator or other mixing device (not shown) may be provided in mixing chamber 54 if desired, to further mix the components of the infusion held there.

Outlet 50 includes a controllable valve or other selectively controllable feed device controlled by controller 36 via connections 44 to meter the concentrate within container 38 at a desired rate in view of the flow rate through pump 28. If desired, a filter 57 may be provided in mixing chamber 54 or between mixing chamber and outlet 22 to further filter the intravenous solution before it is discharged. Filter 57 may filter to a level the same as, greater than, or less than any filter in purifying device. If desired, filter 57 may provide a filtration particle size of about 0.2 microns or smaller.

Depending on the substance in the container 38, the container my use a selectively openable inlet 52 controlled by controller 36 to allow liquid from filter 30 to pass into the container (see arrow a to container 38*d* in FIG. 8) if such is needed for creation of the intravenous solution. Alternatively, inlet 52 can simply be used for filling container 38 as part of the manufacturing or refilling process. If concentrate is to be dispensed into the flow (in mixing channel 55 or mixing chamber 54) then the liquid can pass by but not into the containers (see arrow b along containers 38*a-c* in FIG. 8).

Mixing chamber 54 can accumulate the mixed substances provided from inlet 20 and the cartridges 38*a-d*. If desired, mixing in chamber 54 may be passive, although a pump, actuator, stirrer, etc. may be provided to create a more uniform mixture if needed. Mixing chamber 54 may be for example on the order of 475 ml, but other sizes are possible. Device 10 may employ a gravity feed drip to outlet 22 if the created intravenous solution is to be administered to a patient 56. Alternatively, a pump may be used to remove the solution from mixing chamber, particularly if the created intravenous solution is to be placed in a container 58 for later use, stockpiled, moved a distance from device 10, etc. One-way check valves 59 may be provided generally throughout housing 10 along the flow path to ensure flow moves only forward and no undesired missing or contamination occurs.

Display 18 may include any number of screen images, each having indicators and input devices for facilitating use of device 10. For example, FIG. 1 shows display 18 with an in-use screen image, although alternate screen images may be employed on display 18, such as an initialization image, an override image, single cartridge status information image, a diagnostic information image, etc., as desired.

For example, device 18 in-use image may include information such as a touchscreen with a QWERTY or other keyboard 60 or equivalent alphanumerical input device. Indicators may be provided for battery 62 life and/or AC electrical power (not shown). An indicator may be provided (that may light up or change color, etc. when chosen) for male 64 or female 66 patient. Flow rate indicators 68*a-c* may be provided adjacent concentrate identifiers 70*a-c*. Fullness indicators/time to empty indicators 72*a-d* may be provided adjacent concentrate indicators 74*a-d* and/or 70*a-c*. An indicator 76 showing a patient's weight has been input may be provided, as well as on 78/off 80 indictors for starting and stopping operation of device. It should be understood that some or all of the input output devices may be provided by mechanical buttons, and indicators may be lights such as LED's, LCD's, etc., rather than providing a large touch-screen display 18 covering housing 12. Or smaller screens or touchscreens could be provided for some or all input or information. Also, a remote controller connectable via a wired or wireless connection could be used for some or all input/output functions.

To use device 10 ad hoc with a patient, a user would turn the device on using the on-off switch 34. Display 18 would indicate initialization and readiness to the user. The user could use the touch screen to indicate via touch symbols 64, 66, 76, and others (not shown) such as injury type or severity, general operational and patient parameters, desired medications, source of liquid, etc. Device 10 would then indicate to the user a course of treatment (types of solutions to be provided, dosages, etc.) following algorithms or based on information stored in lookup tables corresponding to the entered information. The user could use an override function, for example by pressing an override indicator (not shown) on display 18, to change the course of treatment, either on the current screen image or on an alternate override screen image.

Once data is entered and a course of treatment is selected, the user can connect a source of liquid S1-S3 to inlet 20 and insert infusion kit 24 into the patient. Infusion kit 24 is then attached to liquid outlet, and a start button is pressed on display 18 to begin the intravenous infusion process. Using display 18 and the information provided thereon, the user can monitor progress of the infusion. As the infusion will most likely be via gravity drip, device should be held upright so that the liquids flow down into chamber 54 and out outlet 22. If desired, an orientation sensor may be provided and information may be provided to the user on display confirming proper orientation for gravity feed. Also, a speaker may be provided for providing information, reminders, warnings, etc., to the user during operation.

After completing an infusion and removing the infusion kit 24 from the patient, the device may be flushed with water and/or other cleaning liquid supplied via inlet in one or more cycles or sequences. To do so, pump 28 operates, but no other substances are fed from cartridges 38*a-e*.

Figure 8:
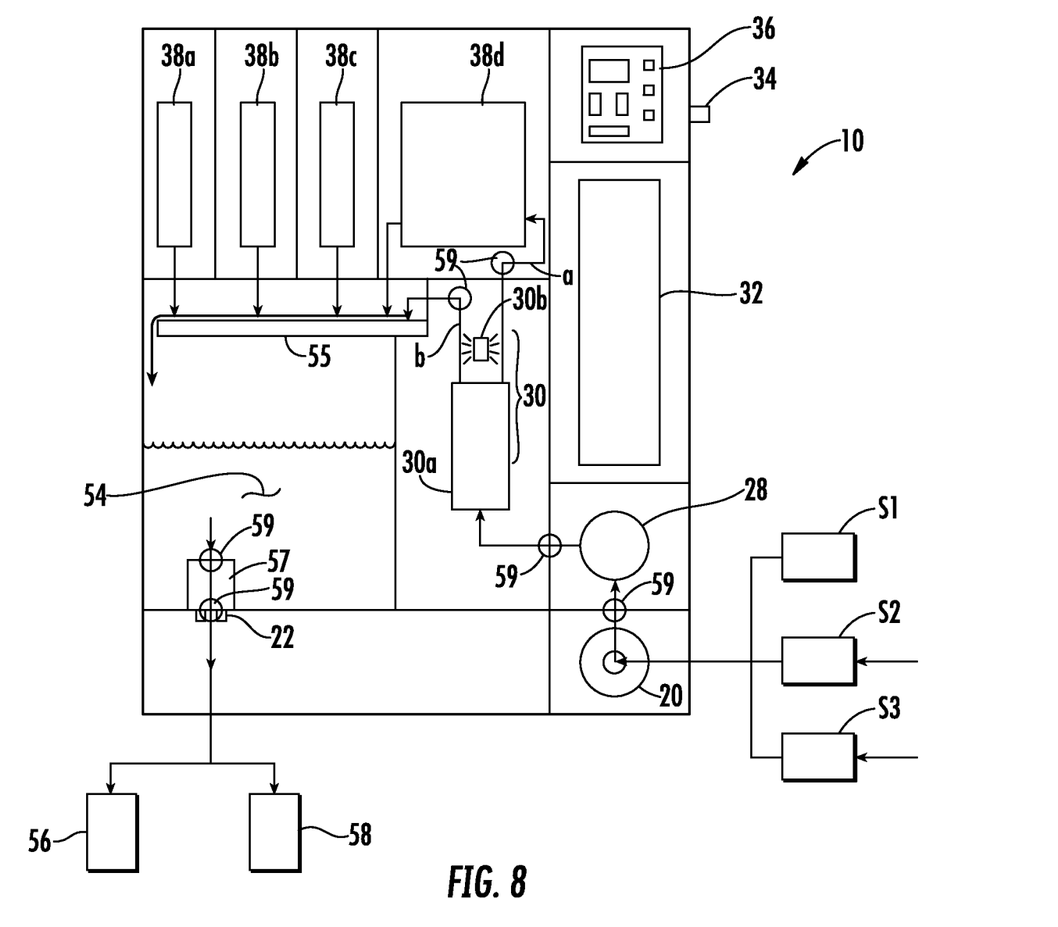
FIG. 8 is a schematic view illustrating the functions, connections and possible uses of different types of devices for producing a medically-deliverable intravenous solution in different environments.
Figure 9:
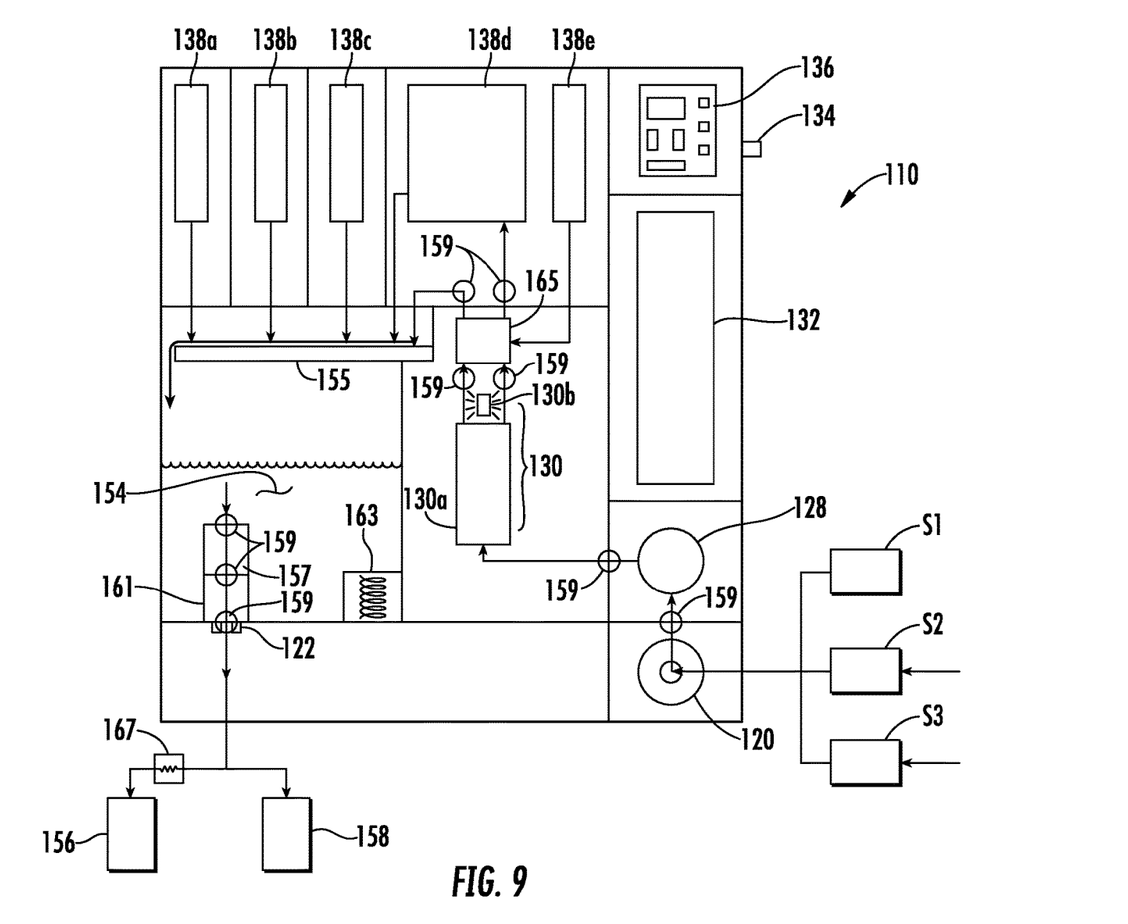
FIG. 9 is a schematic view of a device as in FIG. 9, but having added features and functions.

FIG. 9 shows a modified device 110 having features and functions in addition to those of the device illustrated in FIG. 8. Elements having reference numerals beginning with 100 in FIG. 9 are like or similar to the elements in FIG. 8 having the same last two digits. For sake of brevity the descriptions of all such like and similar parts is not repeated here.

As illustrated, device 110 includes additional elements 138*e*, 161, 163, 165, and 167, along with other connecting and control features, as is described below. Device 110 includes a liquid inlet 120, a liquid outlet 122 and various cartridges 138*a-d*, as above, for metering substances into the liquid. Filtration and purification of the water source S1, S2, S3 can occur at purification device 130 and filter 157. Pumps 128 and 161 can be used to respectively draw liquid into device 110 or for infusion of liquid from mixing chamber 154 into a patient. Pump 161 may this be an infusion pump for pumping the medically deliverable intravenous solution from mixing chamber 154, through filter 157, out of outlet 122 into infusion kit 156. Use of such an infusion pump 161 can be beneficial where gravity assisted (drip) infusion is not possible or is inconvenient.

A heating device 163 may be located in the device so as to heat at least the liquid (S1, S2, S3) upstream of outlet 122. As illustrated, heating device 163 is located so as to heat the medically-deliverable intravenous solution in mixing chamber 154. Heating device 163 could be an electric resistance heater or other type of device. A sensor (which may be located in the same sub-housing as heating device 163 or spaced from it) may be employed in communication with controller 136 for sensing a temperature of the medically-deliverable intravenous solution so that the controller may cause the heating device to provide heat based on the sensed temperature (e.g., to raise it to a desired temperature). Such heating of liquid to be infused may be useful, for example, if a bolus dosing is to be administered to a patient.

A P.H. adjustment chamber 165 may be used, wherein container 138e may be used to supply a desired amount of a P.H. adjusting liquid for adjusting the P.H. of the medically-deliverable intravenous solution. The P.H. adjusting liquid may include, for example, HCl, and P.H. adjustment chamber 165 may be upstream of mixing chamber 154. A sensor (not shown, but which cold be located anywhere between Sources S1, S2, and S3 and chamber 165) may be employed in communication with controller 136 for sensing a P.H. of the liquid supplied by the source of liquid. Controller 136 then causes container 138e to dispense a desired amount of P.H. adjusting liquid based on the sensed P.H communicated by the sensor. Use of such a P.H. adjusting chamber may be useful to lower the P.H., particularly where alternative water sources are being employed with higher P.H. than would be optimal for an infusion.

If desired, intravenous infusion kit 156 may include a sensor 167 in communication with controller 136 for determining a blood pressure of a patient by sensing a line pressure of the medically-deliverable intravenous solution in the infusion kit. Sensor 167 may be employed in the line of infusion kit 156, or at, on, or near) outlet 122 (still considered for present purposes part of infusion kit 156). Controller 136 may thereafter cause device 110 to display the determined blood pressure of the patient on a display (e.g., on an indicator on display 18). Display 18 thus constitutes an input-output device that may be employed for receiving input from a user and for providing operational data information to the user.

With regard to the methods employable by device 110, the dispensing step may include pumping the medically deliverable intravenous solution out of mixing chamber 154, for example using pump 161.

The method may also further include supplying heat upstream of the outlet, for example using heating device 163. If so the supplying heat step may include supplying heat to the medically-deliverable intravenous solution in mixing chamber 154, and/or sensing a temperature of the medically-deliverable intravenous solution before supplying heat based on the sensed temperature of the medically-deliverable intravenous solution The method may further include adjusting a P.H. of the supplied liquid, for example in a P.H. adjustment chamber 165 using a substance from container 138e. If so the adjusting of the P.H. of the supplied liquid may include adding HCl to the supplied liquid in the P.H. adjustment chamber 165, and/or sensing a P.H. of the supplied liquid before adjusting a P.H. of the supplied liquid based on the sensed P.H of the supplied liquid.

The method may further include administering the medically-deliverable intravenous solution to a patient using intravenous infusion kit 156, which may include determining a blood pressure of a patient by sensing a line pressure of the medically-deliverable intravenous solution in the infusion kit, for example via a sensor 167. Such sensed pressure may be displayed on a display 18. The method may also include receiving input from a user and providing operational data information to the user via an input-output device (display 18 or other).

Device(s) 10 and 110 as depicted can be sized and configured to be portable and mobile, and therefore can be placed in a typical first responder kit, emergency vehicle, medical facility, supply closet, military or hunting kit or facility, first aid kit, school, remote location, or carried by a hiker or in a vehicle, etc. If the device is instead being used to create a stockpile of medically-deliverable intravenous solution, it can be made larger, and could still be mobile (such as on a wheeled cart) or could be fixed in place in a building, for example near a source of power and liquid. The created solution could simply be saline solution or equivalents or substitutes with no additional medication, or the created solution can be combinations of such. The stockpiled solution could be used onsite, or could be shipped to alternate sites, as desired. Amounts can be made on-site periodically during down time to stock an emergency vehicle, medical facility, military vehicle, etc.

While preferred embodiments of the invention have been described above, it is to be understood that any and all equivalent realizations of the present invention are included within the scope and spirit thereof. Thus, the embodiments depicted are presented by way of example only and are not intended as limitations upon the present invention. Thus, while particular embodiments of the invention have been described and shown, it will be understood by those of ordinary skill in this art that the present invention is not limited thereto since many modifications can be made. Therefore, it is contemplated that any and all such embodiments are included in the present invention as may fall within the literal or equivalent scope of the appended claims

I claim:

1. A device for producing for immediate intravenous administration to a patient a medically-deliverable intravenous saline solution from a source of water, the device comprising:
    a housing, the housing defining an inlet and an outlet, the inlet attachable to the source of water for receiving water therefrom, the outlet configured for use in immediate intravenous administration of the medically-deliverable intravenous saline solution to the patient;
    a conduit connected to the housing extending from the inlet to the outlet;
    a purification device located within the housing along the conduit downstream of the inlet for purifying the water received from the source of water;
    a pump within the housing for pumping the water through the conduit;
    a container connectable to the housing holding a concentrated intravenous saline solution, the container having an outlet in communication with the conduit;
    a metering device for dispensing the concentrated intravenous saline solution from the container into the water within the conduit; and
    a controller connected to the housing for controlling the pump and the metering device so as to create the medically-deliverable intravenous saline solution from the water and the concentrated intravenous solution within the conduit and to deliver the medically-deliverable intravenous saline solution to the outlet for immediate intravenous administration to the patient.

2. The device of claim 1, further including at least one additional container for supplying a medical liquid and at least one additional metering device for dispensing the medical liquid from the at least one additional container into the water within the conduit.

3. The device of claim 1, further including a pH adjustment chamber along the conduit in the housing, at least one additional container for supplying a pH adjusting liquid, and at least one additional metering device for dispensing the pH adjusting liquid from the at least one additional container into the water in the pH adjustment chamber for adjusting a pH of the medically-deliverable intravenous saline solution delivered to the outlet of the housing.

4. The device of claim 3, wherein the pH adjusting liquid includes HCl, and wherein the pH adjustment chamber is upstream of a mixing chamber.

5. The device of claim 3, further including a sensor in communication with the controller for sensing a pH of the water supplied by the source of water, the controller causing the at least one additional metering device to dispense the pH adjusting liquid based on a sensed pH communicated by the sensor.

6. The device of claim 1, further including a water supply container for supplying the water, the water supply container having an outlet connected to the inlet of the housing.

7. The device of claim 1, further including a sensor for sensing a flow of the water in the conduit.

8. The device of claim 7, wherein the sensor sends a signal to the controller, and the controller operates the pump and the metering device based on the signal to create the medically-deliverable intravenous saline solution.

9. The device of claim 1, further including a mixing chamber along the conduit downstream of the purification device and the metering device and upstream of the outlet, the water pumped by the pump and the concentrated intravenous saline solution dispensed by the metering device being housed in the mixing chamber before passing through the outlet.

10. The device of claim 9, further including a mixing channel between the metering device and the mixing chamber, the pump pumping the water into the mixing channel and the metering device dispensing the concentrated intravenous saline solution into the mixing channel.

11. The device of claim 9, further including a filter along the conduit between the mixing chamber and the outlet.

12. The device of claim 9, further including a heating device located in the housing so as to heat at least the water upstream of the outlet.

13. The device of claim 12, further including a sensor in communication with the controller for sensing a temperature of the medically-deliverable intravenous saline solution, the controller causing the heating device to provide heat based on a sensed temperature communicated by the sensor.

14. The device of claim 9, further including an infusion pump located in the housing for pumping the medically-deliverable intravenous saline solution out of the outlet.

15. The device of claim 1, wherein the device includes an intravenous infusion kit in communication with the outlet for use in the immediate intravenous administration of the medically-deliverable intravenous saline solution to the patient.

16. The device of claim 15, wherein the device includes a sensor in communication with the controller for sensing a line pressure of the medically-deliverable intravenous saline solution in the infusion kit.

17. The device of claim 1, further including an input-output device in communication with the housing for receiving input from a user and for providing operational data information to the user.

18. The device of claim 1, wherein the housing is configured for removable attachment of the container and replacement of the container when the all concentrated intravenous saline solution in the container has been dispensed by the metering device.

19. A kit including the device of claim 18, wherein the device includes at least two of the containers of the concentrated intravenous saline solution.

20. The kit of claim 19, further including at least one additional container for supplying a medical liquid and at least one additional metering device for dispensing the medical liquid from the at least one additional container into the water within the conduit.

21. The device of claim 1, wherein the housing supports the conduit, the purification device, the pump, the container, the metering device, and the controller in a portable unit, and wherein the device includes an intravenous infusion kit in communication with the outlet for use in the immediate intravenous administration of the medically-deliverable intravenous saline solution to the patient.

22. The device of claim 1, wherein the medically-deliverable intravenous saline solution includes one of a normal saline solution and a hypertonic saline solution.

23. The device of claim 1, wherein the concentrated intravenous saline solution includes one of a concentrated normal saline solution and a concentrated hypertonic saline solution.

24. The device of claim 1, wherein the purification device includes a filter.

25. The device of claim 24, wherein the filter has multiple sequential stages, wherein a more downstream one of the stages is configured for a finer filtration than a more upstream one of the stages.

26. The device of claim 1, wherein the purification device includes a UV radiation source.

* * * * *